US008071949B2

(12) United States Patent
Majewski et al.

(10) Patent No.: US 8,071,949 B2
(45) Date of Patent: Dec. 6, 2011

(54) HIGH-RESOLUTION SINGLE PHOTON PLANAR AND SPECT IMAGING OF BRAIN AND NECK EMPLOYING A SYSTEM OF TWO CO-REGISTERED OPPOSED GAMMA IMAGING HEADS

(75) Inventors: Stanislaw Majewski, Yorktown, VA (US); James Proffitt, Newport News, VA (US)

(73) Assignee: Jefferson Science Associates, LLC, Newport News, VA (US)

( * ) Notice: Subject to any disclaimer, the term of this patent is extended or adjusted under 35 U.S.C. 154(b) by 336 days.

(21) Appl. No.: 12/321,667

(22) Filed: Jan. 23, 2009

(65) Prior Publication Data

US 2010/0187425 A1    Jul. 29, 2010

(51) Int. Cl.
*G01T 1/166* (2006.01)
(52) U.S. Cl. .................................. 250/363.05
(58) Field of Classification Search ............... 250/363.05
See application file for complete search history.

(56) References Cited

U.S. PATENT DOCUMENTS

| 5,337,760 | A  | * | 8/1994 | Nichols ............................ 5/637 |
| 6,194,725 | B1 | * | 2/2001 | Colsher et al. ............ 250/363.05 |
| 6,794,653 | B2 |   | 9/2004 | Wainer et al. |
| 7,381,961 | B2 |   | 6/2008 | Conwell |
| 2008/0284428 | A1 | * | 11/2008 | Fiedler et al. ................. 324/307 |

OTHER PUBLICATIONS

Seidel et al. Performance characteristics of position-sensitive photomultiplier tubes combined through common X and Y resistive charge dividers, 1999 Nuclear Science Symposium Conference Record, vol. 3 (Oct. 1999), pp. 1488-1489.*
Azman et al. A nuclear radiation detector system with integrated readout for SPECT/MR small animal imaging, 2007 Nuclear Science Symposium Conference Record, vol. 3 (Nov. 2007), pp. 2311-2317.*
Studenski et al. Performance evaluation of a small field-of-view, mobile PET/SPECT system, 2007 Nuclear Science Symposium Conference Record, vol. 5 (Nov. 2007), pp. 3770-3773.*

* cited by examiner

*Primary Examiner* — David Porta
*Assistant Examiner* — Shun Lee

(57) ABSTRACT

A compact, mobile, dedicated SPECT brain imager that can be easily moved to the patient to provide in-situ imaging, especially when the patient cannot be moved to the Nuclear Medicine imaging center. As a result of the widespread availability of single photon labeled biomarkers, the SPECT brain imager can be used in many locations, including remote locations away from medical centers. The SPECT imager improves the detection of gamma emission from the patient's head and neck area with a large field of view. Two identical lightweight gamma imaging detector heads are mounted to a rotating gantry and precisely mechanically co-registered to each other at 180 degrees. A unique imaging algorithm combines the co-registered images from the detector heads and provides several SPECT tomographic reconstructions of the imaged object thereby improving the diagnostic quality especially in the case of imaging requiring higher spatial resolution and sensitivity at the same time.

19 Claims, 4 Drawing Sheets

HIGH-RESOLUTION SINGLE PHOTON PLANAR AND SPECT IMAGING OF BRAIN AND NECK EMPLOYING A SYSTEM OF TWO CO-REGISTERED OPPOSED GAMMA IMAGING HEADS

The United States of America may have certain rights to this invention under Management and Operating contract No. DE-AC05-06OR23177 from the Department of Energy.

FIELD OF THE INVENTION

This invention relates to SPECT imaging and more particularly to a compact and mobile high resolution SPECT imaging system for imaging the head, brain, and neck areas of a patient.

BACKGROUND OF THE INVENTION

Brain disease is becoming more prevalent in the aging population because of increased life span and Alzheimer's, Parkinson's, other dementias, and brain cancer will increase as US and European populations continue to age. Approximately 4,000,000 people in the U.S. have Alzheimer's disease. The US alone is expected to have 15 million Alzheimer's cases by 2050. Also an estimated 1.5 million people in the US have Parkinson's. Neurological brain disease affects 1% of Americans over 60 and each year there are 100,000 new cases. Diagnostic analysis of brain function represents an area of unmet need in the current imaging technology. Physicians require more specific and accurate information about brain function in addition to anatomy in order to diagnose a condition, prescribe treatment, and monitor results of intervention and treatment. Promising new drug therapies for Alzheimer's disease have been developed that can slow the progression of the disease. Nuclear medicine currently provides several molecular imaging modalities to assist with the assessment of brain function: Positron Emission Tomography (PET), Single Photon Emission Computed Tomography (SPECT), and planar limited-angle tomography or simple planar single gamma imaging.

From the point of view of brain biology and imaging performance, including the physics of the process and imaging technique, PET is the first choice for the molecular brain imaging tasks for several reasons, including: 1) 18F-FDG brain imaging already serves as a sensitive method for diagnosis of Alzheimer's, 2) Pittsburgh Compound B (PIB) biomarker is expected to further improve early diagnosis of Alzheimer's, 3) many new PET radiopharmaceuticals for brain function imaging are presently under development to diagnose conditions before symptoms appear, 4) 4-5 mm resolution provided by current clinical PET scanners is less than half of that provided by clinical SPECT systems, and 5) the physical limit of the PET technique is around 1-2 mm while the typical spatial resolution obtained in SPECT imaging is about 10 mm due to the physical limits of mechanical collimators. However, at the current time PET's availability and cost are obstacles to fast widespread introduction while single photon labeled biomarkers can be made available in most practical situations due to their longer half-lives, no need for nearby production centers, and lower cost.

Tc-99m is the most popular label used in nuclear medicine with photon (gamma) emissions at ~140 keV and with a convenient half-life of about 6 hours. The major problem associated with the single photon imaging procedure is that the characteristic gamma radiation from Tc-99m undergoes substantial absorption when traversing tissues such as brain. As a result for Tc-99m, the gamma ray flux, and the associated imaging signal in the gamma camera, coming from the sector of the head/neck away from the detector is much more attenuated than the gamma rays originating in the front part of the head.

With proper collimators and shielding, distribution of other single photon labels can be imaged such as I123, In111, Lu177, or I131. Except I123 (159 keV gamma emission), the three listed beta emitters are used in radiation treatment of cancer, also known as brachytherapy. In principle, therefore, the proposed method can also improve imaging of cancerous tissue in the brain/neck during treatment.

Neurological disorders that can be diagnosed by SPECT include traumatic brain injury, Alzheimer's, Attention Deficit Hyperactivity Disorder (ADHD), anxiety disorders, autism, bipolar disorder, depression, and obsessive-compulsive disorder.

What is needed therefore, is a mobile dedicated SPECT brain imager capable of producing high resolution images of the entirety of the patient's head, brain, and neck area. The dedicated imager geometry will include a reduced loss of imaging signals, which is commonly associated with conventional SPECT imagers, coming from the sector away from the detector as a result of attenuation of the gamma rays. By using SPECT imaging, the brain imager will take advantage of the longer half-lives of SPECT biomarkers which are more easily available at a lower cost than comparable PET biomarkers.

SUMMARY OF THE INVENTION

The present invention is a compact, mobile, dedicated SPECT brain imager that can be easily moved to the patient to provide in-situ imaging, especially when the patient cannot be moved to the Nuclear Medicine imaging center. As a result of the widespread availability of single photon labeled biomarkers, the SPECT brain imager can be used in many locations, including remote locations away from medical centers. The SPECT imager improves the detection of gamma emission from the patient's head and neck area. The SPECT imager improves the diagnostic quality using single gamma imaging modality especially in the case of imaging that requires higher spatial resolution and sensitivity at the same time.

OBJECTS AND ADVANTAGES

Several advantages are achieved with the high-resolution single photon planar and SPECT brain imager of the present invention, including:

(1) The field of view coverage is significantly improved (about 20 cm×15 cm) over conventional SPECT brain imagers by providing two identical compact lightweight gamma imaging detector heads mounted on a rotating gantry and precisely mechanically co-registered to each other at 180 degrees (placed opposite to each other). The detector heads are placed on both sides of the patient and mechanically affixed relative to each other, with the patient's brain or neck fully encompassed by the resulting active field of view coverage.

(2) The parallel-hole collimators mounted on the two gamma cameras are precisely mechanically aligned, with accuracy of alignment validated with point and linear radioactive sources.

(3) Two individually produced series of angular projections of the imaged region of the patient's head or neck in both detector heads will be obtained using the stepping or continuously rotating mechanical gantry, and are processed as one set of projection images by special imaging algorithm involving multiplication or other combined treatment of the pre-processed co-registered images from both imagers, for each angular projection.

(4) The projection images obtained from the individual detector heads and the combined images are used to obtain three SPECT tomographic reconstructions of the object with the combined images serving as the standard set and the individual images providing additional information, as necessary. As an example, the individual images contain linear information on the radioactivity uptake ratios, while the combined images are highly non-linear.

(5) The system made of two sets of the above co-registered detector heads can be used in several modes including a planar mode for stereotactic viewing to provide two simultaneous complementary dynamic views of the head/neck region, to provide two independent SPECT scans, or utilizing each pair to provide half of the angular views that will be combined to produce one combined set of tomographic SPECT images.

(6) The patient can be lying down on a bed, sitting straight in a chair, or optimally sitting in a chair in a reclined position in a chair to limit movements of the patient's head while providing patient comfort.

(7) The patient's head will be attached to the imaging bed or chair to minimize head movements during scan but not to cause large discomfort.

(8) The imaging bed, chair and/or imager gantry will allow for positioning of the central imaging plane at the proper height at the neck/head region to provide optimized imaging of the region of interest.

(9) Following new imaging standards in high resolution imaging, position of the patient's head is constantly monitored by an optical monitoring system to correct the SPECT data for head movements during the scan.

(10) The two compact detector heads can employ an array of compact position sensitive PMTs, but also the novel silicon photomultipliers (SiPMTs) making the system even more compact and potentially even more robust.

(11) Implementation of SiPMTs and providing MRI-compatible shielding, collimators and other materials, which are immune to strong magnetic fields, permit insertion of the imager into an MRI magnet to achieve simultaneous dual-modality imaging, including fMRI-SPECT which combines two functional imaging modalities to study brain function.

These and other objects and advantages of the present invention will be better understood by reading the following description along with reference to the drawings.

Figure 1:
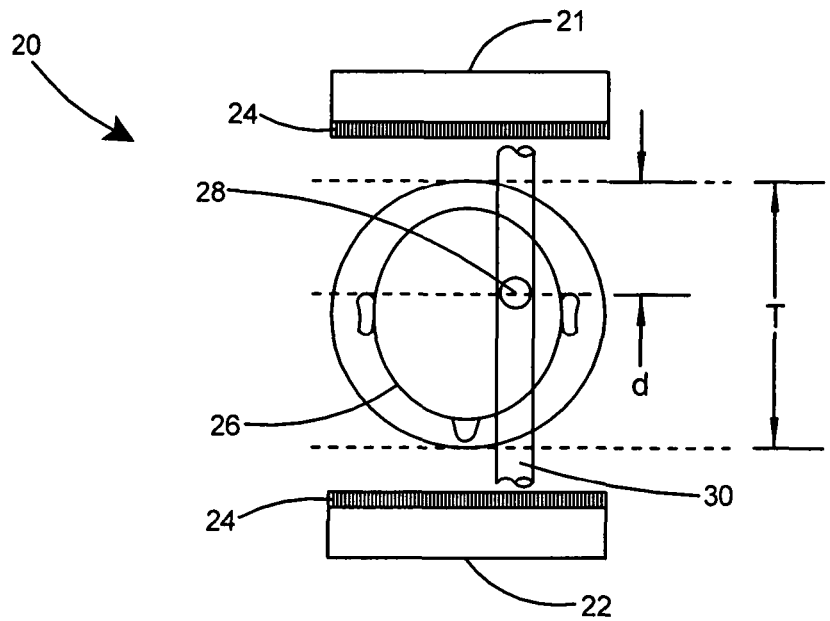
FIG. 1 is an overhead view from above the patient's head of a brain imaging system according to the present invention including the geometrical parameters of the formula used to determine the number of gamma rays detected by each camera.

INDEX TO REFERENCE NUMERALS IN DRAWINGS 20 compact opposed head brain imaging system, first embodiment
21 first detector or gamma camera
22 second detector or gamma camera
24 parallel-hole collimator
26 patient's head
28 head/neck/brain sector
30 projective tube of gamma rays reaching the detectors
40 detector head, preferred embodiment
42 flat panel multi-pad PMT
44 optical spreader window
46 scintillation array
48 window
50 reflective strip
52 dead region
60 compact dual opposed head imaging system, preferred embodiment
62 first pair of co-registered gamma detector heads
64 second pair of co-registered gamma detector heads
66 detector head
68 ring plate
70 patient's head

DETAILED DESCRIPTION OF THE INVENTION

During conventional SPECT imaging, a series of images or projections are acquired from different angular detector head positions. Imaging heads are mounted on a rotating gantry. Each sector of the patient's head or neck has better visibility from the directions of closest approach to that sector, with the exception of the inner sectors of the head or neck that are equally distant from all directions. The imaging signal in the gamma camera from the inner sectors is much more attenuated and as a result image reconstruction for those sectors is poor.

A substantial improvement can be obtained in SPECT by employing the concept of combining projection images for each angular view from two opposed and co-registered gamma imaging heads, before implementing 3D tomographic reconstruction algorithm of the object. In addition, computer modeling of the absorption and spatial resolution effects, as well as subsequent correction of the collected data, would improve the quality of reconstructed 3D images.

In the present state of the art, scintigraphy, or single photon gamma imaging, of patients is performed with standard nuclear medicine cameras and it suffers from poor sensitivity for small features such as lesions under 1 cm in diameter, and especially objects located away from the gamma camera surface. The main contributing factor to this poor performance is poor spatial resolution during imaging due to the large distance between the sector or lesion and the detector head. As a result, patient studies completed with conventional large field of view (FOV) cameras suffer from poor resolution due to large target-to-collimator distances (TCD). Since resolution decreases as a function of object distance, the TCD becomes the primary factor for spatial resolution and therefore for lesion detection sensitivity. Small FOV imaging heads can be in principle placed very close to the patient's head to improve spatial resolution by minimizing the TCD. However, lesion-to-camera distance still has a strong impact on lesion detection, and even these dedicated instruments show substantial sensitivity variation depending on lesion position within the object (head, neck, etc). By incorporating a second detector on the opposite side of the patient's head, we are guaranteed to minimize the TCD for all cases.

The subject of our invention is a substantial remedy to the theoretically expected and clinically observed limitation in the detection of Tc-99m gamma emission from the patient's head/neck. This limitation adversely impacts the diagnostic quality of all single gamma imaging modalities but especially in the case of imaging requiring higher spatial resolution and sensitivity at the same time (often required during brain imaging).

The compact, mobile, dedicated SPECT brain imager of the present invention can be moved to the patient (ER, ICU, hospital bed, outpatient center) to provide in-situ imaging, especially when the patient cannot be moved to the Nuclear Medicine imaging center. Due to wide-spread availability of single photon labeled biomarkers, as compared to PET, a SPECT brain imager can be used in many locations, also far away from medical centers. A high efficiency, high resolution (about 5 mm), and economical dedicated SPECT brain imager according to the present invention can have an important impact on early detection of brain disease or condition (for example trauma) and on therapy planning and monitoring. The higher spatial resolution of the imager maintains sensitivity due to the special co-registered dual-head design. The brain imager of the present invention detects smaller abnormalities and enables earlier and more accurate diagnosis of brain diseases or conditions than standard single-photon imagers. The brain imager utilizes high-performance molecular imaging modality in conjunction with recently introduced biomarkers to improve early diagnosis of brain diseases such as dementia.

The brain SPECT imager of the present invention includes a dedicated lightweight mobile gantry for rotational and potentially translational scan, depending on the angular coverage by the imager modules (one or two imaging pairs) and the width of the imaging slice (5-20 cm). The brain SPECT imager can provide optional fast continuous dynamic scan for high-quality complete angular sampling, fast planar imaging, standard, or limited-angle SPECT imaging. The compact geometry enables close positioning of imager and gantry to the patient's head/neck with improved resolution and/or sensitivity. The distance between the detector heads can be adjusted to accommodate different situations, such as a chair or bed, with different sized patient heads. A compact geometry allows flexible imaging geometries with several options for the patient, including lying down on a bed or sitting in a static or rotating chair. All system elements including the rotating gantry, bed, and chair can be mobile for easy transfer between locations, storage, or easy installation on a vehicle. A head/neck monitoring system to correct for head/neck movements during scans can be included in the system. A data processing station with readout electronics and control and a dedicated computer can be either installed in a separate mobile wheeled cabinet or incorporated/attached to the gantry or to the bed or chair.

The proposed co-registered dual-head single photon brain imager concept can also be used in principle for other parts of the patient's body such as extremities, neck and thyroid, and even breast if reconfigured on a different gantry and fitted with optimal collimators.

With reference to FIG. 1, there is shown an overhead view explaining the geometrical parameters of the approximate formula used herein to demonstrate the improvement obtained by the use of co-registered detectors. The brain SPECT imager 20 of the present invention operates under the principle of co-registered dual-sided imaging using standard gamma cameras. The geometry includes two identical gamma cameras 21 and 22 with identical and co-linear parallel-hole collimators 24 placed on opposite sides of a patient's head 26. The geometrical parameters of the approximate formula applied in the equations (1) and (2) herein below are shown in FIG. 1. The head/neck/brain sector 28 with radiation activity A is at depth d below the head/neck surface/skin measured in the direction of camera or detector 21. Object thickness at the particular cross-section level is T. The gamma rays reaching the two detectors 21 and 22 from the selected head/neck/brain sector 28 are approximately contained within the projective tube 30, perpendicular to the front detector surfaces, and of a transversal size of the object sector, due to the use of parallel-hole collimators 24 in the preferred arrangement.

If the total radioactivity per unit time in the head/brain/neck segment is A, then following the simultaneous acquisition of the two planar images, the number of gamma rays detected by each camera 21 and 22 from that head/neck segment can be approximated by:

$$N_{21} = \epsilon_{21} t A \exp[-\mu d]$$

$$N_{22} = \epsilon_{22} t A \exp[-\mu(T-d)] \quad (1)$$

where $\epsilon_1$ and $\epsilon_2$ are the practical detection efficiencies of cameras 1 and 2 respectively (including absorption such as lungs, bones, etc), t is the acquisition time in seconds, $\mu$ is the linear attenuation coefficient of tissue in $cm^{-1}$, d is the depth in cm of the object sector under the surface of the head/neck and measured in the direction of the camera 1 surface, and T is the object thickness in the relevant projection plane and direction, in cm.

Both cameras provide two complementary projection views and corresponding measured activity rates of the head/brain/neck sectors. Both measured activity rates are real activity rates lowered by the attenuation and collimation factors. While the collimation effect on measured activity is quite independent from the distance to the particular object sector, the attenuation effect lowers the measured signal as a function of the distance of the particular head/brain/neck sector from the object surface (distance d). However, if the pixel values of the two co-registered images obtained in the same time bin are multiplied on a pixel-by-pixel basis, resulting in a single product image per each time bin, then the product image signal value from the object segment of interest can be approximated by the following formula:

$$N_{21} N_{22} = \epsilon_{21} \epsilon_{22} t^2 A^2 \exp[-\mu T] \quad (2)$$

Equation (2) shows that the effect of object segment depth d is removed from the formula, with the remaining absorption effect expressed by the head/neck thickness T at that head/neck imaging slice level, i.e. the detection sensitivity is much more uniform across the whole object volume and higher than for any of the two individual views when used separately, or even when summed. The optimal image multiplication or combination formula should involve more precise physics modeling of the object (head or neck), but even this simplified mathematical description shows the main feature and power of the co-registered imaging.

The brain SPECT imager of the present invention improves brain imaging and diagnoses by using two co-registered (pixel-by-pixel) series of dynamic images obtained from two opposed (set at 180 degree relative to each other) gamma imaging heads in order to maximize uniformity of detection sensitivity of activity in the head/brain/neck such as blood flow or perfusion, or other reasons for specific uptake in the tissues of the head/brain/neck over the whole head/neck volume, with minimization of radiation absorption effects.

A normalization/image fusion technique is implemented pixel-by-corresponding-pixel to increase the signal for any object region viewed in two views or images obtained from two opposed detector head positions. The detector heads will be typically mounted on a rotating gantry to obtain a complete set of angular views of the head and/or neck over 180-360 degrees, to subsequently produce a 3D tomographic reconstruction of the object.

To achieve the required precise and unique one-to-one detector pixel correspondence the two detector head positions are geometrically aligned to better than 1 mm. Different formulas can be used for pixel-per-pixel combined angular views from the two cameras. It is critical to combine most efficiently the two images from the double-sided imaging. In addition to summed and multiplied images, other more sophisticated options can include weighing of the two corresponding pixel values before combining their values or even modeling the physical situation with absorption and resolution regression formulas depending on the location of the particular sector of the head and/or neck. Iterative techniques are employed to extract the best information about the object's structure and the biomarker's uptake distribution.

As compared to conventional SPECT imagers, the combined pixel-by-pixel image from both detectors presents much more uniform sensitivity to the dynamics of blood flow or uptake throughout the brain, or in the neck region. The co-registered dual-head imaging system of the present invention enhances the detection signal and detection of small image features through first-order correction for the gamma absorption effect (as shown in formula (2) above). For each projective view of the object the co-registered dual-head imaging system also enhances the detection signal and detection of small image features by 1) increasing the statistical strength of the signals (Signal-to-Noise ratio (S/N)) via correlation of two statistically independent signals measured at the same time by two cameras, and 2) increasing the contrast of image features (hot spots, etc) via combination (multiplication, etc.) of two images measured at the same time by two cameras.

The signal increase provided by the co-registered dual-head imaging system of the present invention is typically non-linear (for example when using pixel-per-pixel image multiplication), and, therefore, cannot be used to extract uptake ratios for different regions of interest (ROIs) but it strongly enhances visibility of ("sharpens") structures and emphasizes the distribution's non-uniformity and, therefore, detection of abnormal biomarker uptake patterns (such as seen in Alzheimer's, trauma, cancer, and other disease conditions).

Several imaging technologies can be implemented in a co-registered dual-head imaging system according to the present invention. A preferred embodiment includes a scintillator as a sensor/energy converter of the gamma rays that pass through the mechanical collimator (typically lead, tungsten, or alloys of these materials), while different photodetectors will serve as detectors of the scintillation light produced by the absorbed gamma rays in the scintillator. The scintillator can be made of pixelated or plate crystal materials such as NaI(Tl), CsI(Tl), CsI(Na), GSO, LaBr3, and others. Thickness of the scintillation material must offer enough stopping power for the gamma rays of a particular energy (for example 140 keV emitted by the Tc99m label) and is typically from a few millimeters to a couple of centimeters.

The photodetector part can be a standard or multi-element photomultiplier, position sensitive, flat panel or microchannel plate based photomultiplier, avalanche photodiode arrays or large-size avalanche photodiodes with resistive etc. readout, and different variants of the novel so called Silicon photomultiplier.

An especially preferred embodiment of the compact dual opposed head imager system using a present day technology is based on an array of 16 Hamamatsu H8500 flat panel multi-pad position sensitive PMTs arranged in a 4×4 array and coupled to 0.6-1.2 cm thick Saint Gobain Crystals and Detectors NaI(Tl) scintillator pixel array with 2 mm-5 mm pixel size. This configuration is optimized for 140 keV energy photons from Tc-99m. Other multi-element PMT types such as Burle 85011-501, available from Burle Industries of Lancaster, Pa., and Photonis XP 1470, available from Photonis USA, Inc. of Sturbridge, Mass., can also be used in the gamma detector heads. The H8500 PMTs are available from Hamamatsu Corporation of Bridgewater, N.J. The Saint Gobain Crystals and Detectors are available from Saint-Gobain Crystals of Hiram, Ohio.

Figure 2:
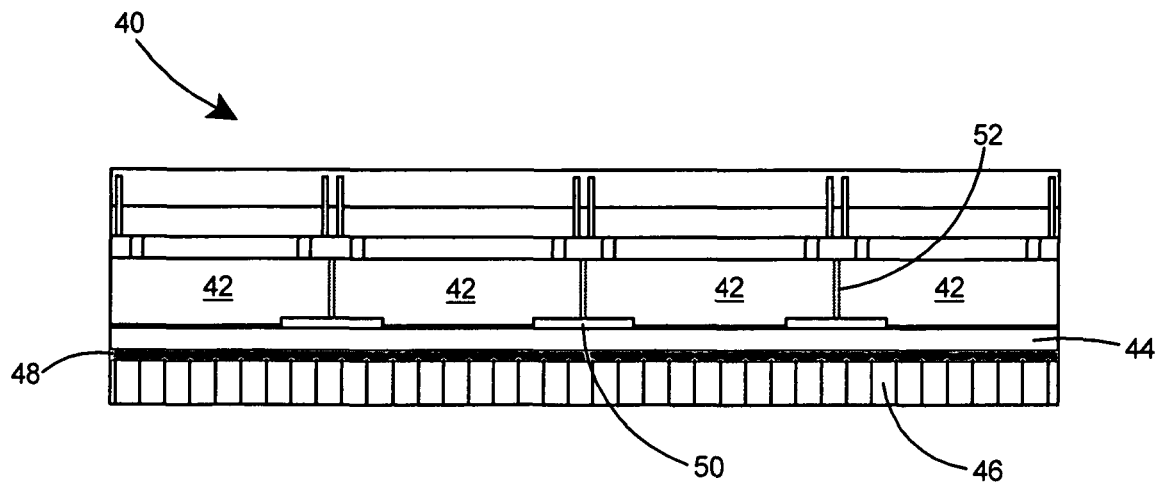
FIG. 2 is an example of a camera head construction based on an array of flat panel multi-pad photomultiplier tubes according to the present invention.

With reference to FIG. 2 there is shown the preferred embodiment of a detector head 40 for use in a co-registered dual-head imaging system according to the present invention. The detector head sensor components include a compact multi-pad PMT arrangement. The camera head 40 construction is based on an array of 16 (4×4) Hamamatsu H8500 flat panel multi-pad PMTs 42 with attached electronics, coupled through optical spreader window 44 to a scintillation array 46 encapsulated behind a window 48. Reflective strips 50 are placed in the dead regions 52 between the PMTs 42 to improve scintillation light collection from the approximately 4 mm wide dead regions 52. The shielding and the collimator in front of the scintillation array 46 are not shown in this sketch.

Each single-head imager, using the compact multi-pad PMT detector head arrangement as shown in FIG. 2, can operate with rate capability of at least 250 kHz. The high rate capability is the result of the design of the instrument including the capability of operating in parallel digital data flow mode for transferring digitized information from the digital imaging camera detector. Conventional gamma cameras currently used in medical practice have intrinsic rate capability limited to less than about 100 kHz due in part to their slow front-end electronics and data acquisition systems.

A second and preferred embodiment of the detector heads, compact and lighter than the first embodiment, includes a detector head in which the multi-pad PMTs are replaced with Silicon PMTs. Silicon PMTs are available from several manufacturers including SensL USA of Mountain View, Calif., Radiation Monitoring Devices, Inc. of Watertown, Mass., Zecotek of Toronto, Canada, and Hamamatsu Corporation of Bridgewater, N.J. Additionally, a non-scintillator based imager head can be based on Cadmium Telluride or Cadmium Zinc Telluride physically or electronically pixelated gamma sensors.

Figure 3:
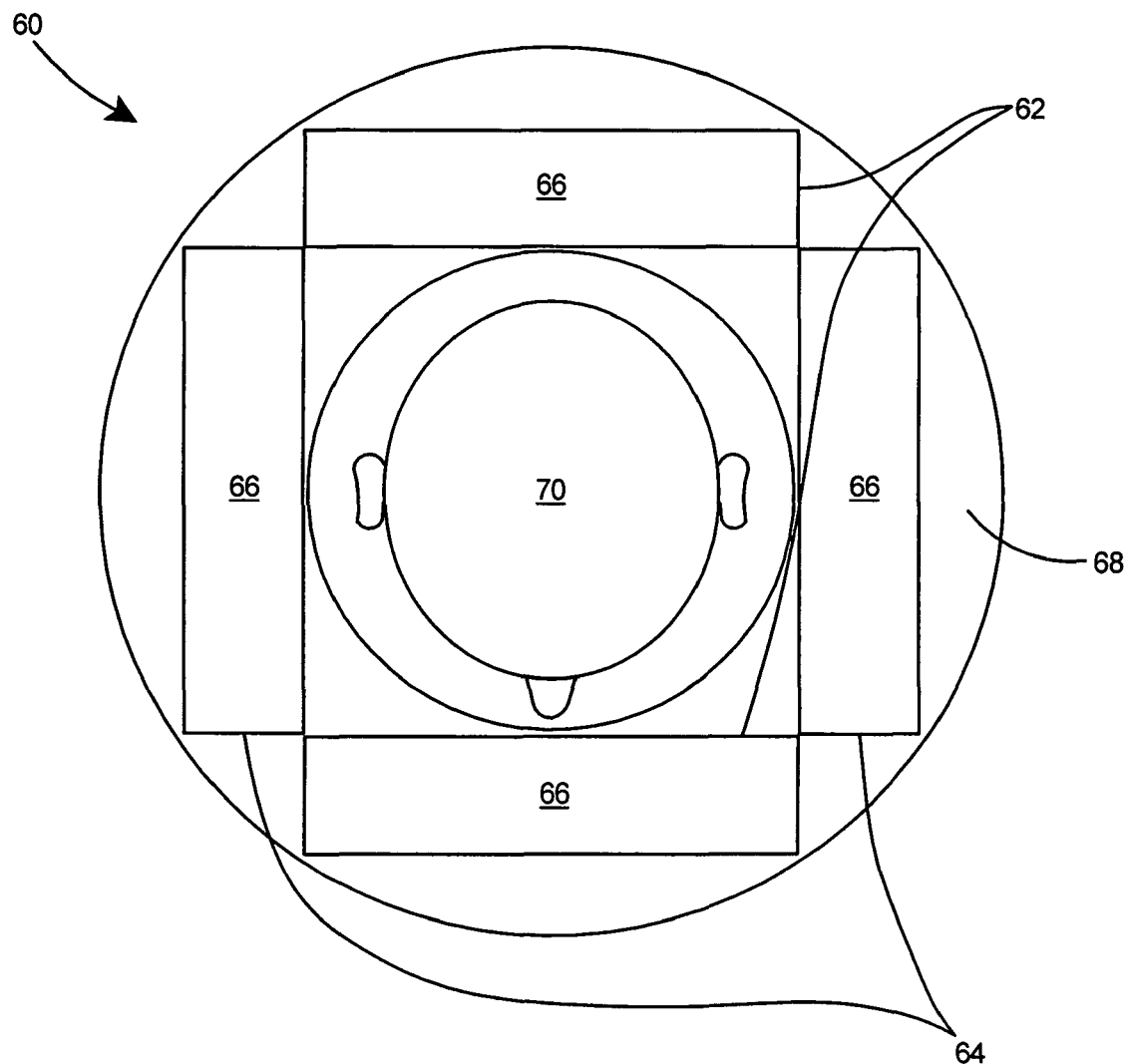
FIG. 3 is an overhead view of two pairs of compact opposed co-registered gamma imagers with relative angles close to 90 degrees and with the detector heads mounted on a ring plate of a rotating gantry.

Referring to FIG. 3, the preferred embodiment of the compact dual opposed head imager system 60 includes two pairs 62 and 64 of co-registered gamma detector heads 66. The two pairs 62, 64 of compact opposed co-registered gamma imagers 66 can provide stereotactic view of the head/neck with relative angles close to 90 deg. The detector heads 66 are mounted on a ring plate 68 of a rotating gantry. The angles and positions of the detectors 66 relative to the patient's head 70 and relative angles between the two pairs 62 and 64 are to some extent flexible and adjustable within the mechanical limitations dictated by the size of the detector heads 66 and associated mounting gear. In addition to offering more optimal SPECT imaging, the simultaneous dynamic recording of two planar stereotactic views of the head/neck can provide depths information to disentangle contributions from overlapping (in one of the views) sectors of the head/neck. Based on these two complementary views, the software can de-convolve the overlapping contributions based on a dynamic model. The net result is a simple yet powerful single-photon imaging system to quickly assess some brain imaging functions, such as first path and other cases of imaging of dynamics of the blood flow, that do not require detailed tomographic information provided by SPECT.

The demonstration of the opposed dual-head concept applied to the breast imaging scenario was performed using phantom tests. The opposed dual-head concept was demonstrated on a breast using phantom tests. Some of the results obtained in these studies are relevant to the head/neck imaging scenario. Experiments performed with soft-tissue equivalent phantoms clearly demonstrated the improvement of the dual-sided imaging over single-sided imaging. In the last sub-section, the results of initial and very recent studies performed with a brain phantom are shown. Several types of collimators were used in the experiments with varying sensitivity and resolution parameters.

Tables 1 and 2 include parameters and measured performances of a set of collimators used in the experiments with compact imaging cameras. Table 1 includes collimator parameters and Table 2 includes measured collimator sensitivity for two imaging energy windows.

TABLE 1

Collimator parameters

| | Hole Diameter (mm) | Height (mm) | Septa (mm) |
|---|---|---|---|
| Collimator 1 | 1.397 | 27.000 | 0.203 |
| Collimator 2 | 1.575 | 21.006 | 0.267 |
| Collimator 3 | 1.778 | 19.990 | 0.305 |
| High Res. | 1.243 | 27.904 | 0.241 |
| Tungsten | 1.25 Square | 17.800 | 0.200 |

TABLE 2

Measured collimator sensitivity for two imaging energy windows.

| | +/−10% WINDOW | −2.5, +30% WINDOW |
|---|---|---|
| Collimator 1 | 131 cpm/µCi | 99 cpm/µCi |
| Collimator 2 | 242 cpm/µCi | 178 cpm/µCi |
| Collimator 3 | 328 cpm/µCi | 244 cpm/µCi |
| High Res. | 93 cpm/µCi | 72 cpm/µCi |
| Tungsten | 299 cpm/µCi | 220 cpm/µCi |

Figure 4:
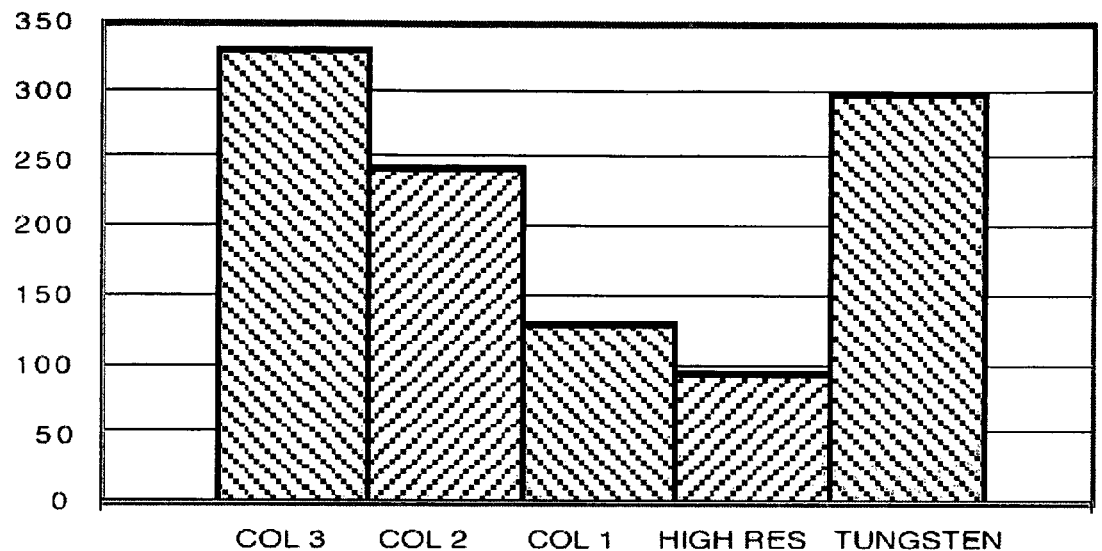
FIG. 4 is a graph depicting the comparative sensitivity measured of five selected collimators for +/−10% energy window.
Figure 5:
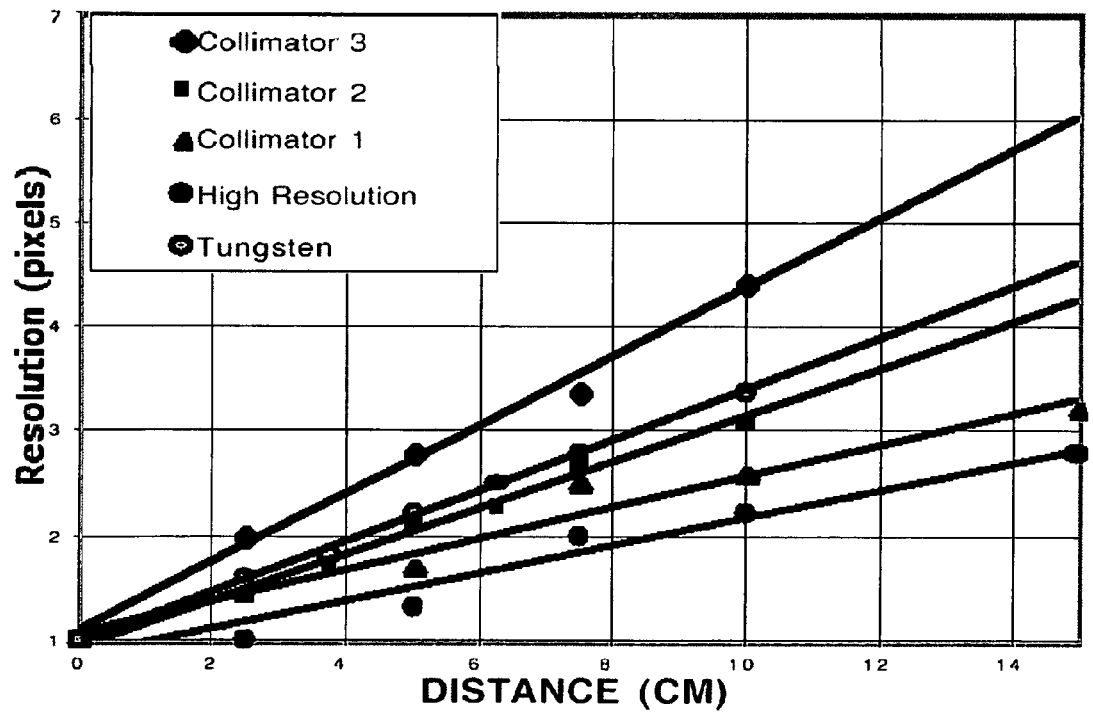
FIG. 5 is a graph depicting the detector extrinsic spatial resolution with various collimators according to the present invention as a function of distance from the detector surface.

The comparative sensitivity measured for the five selected collimators as presented in Table 2 for a +/−10% energy window are shown graphically in FIG. 4. Additionally, FIG. 5 depicts an example of detector extrinsic spatial resolution as a function of distance from the detector surface using the system resolution with various collimators from Table 1. Each line represents a linear fit through the data points. Vertical scale is in scintillation pixels (1 pixel=3.3 mm).

Individual thin capillaries, less than 1 mm diameter, and sets of capillaries filled with radioactive solution were used to measure the spatial resolution of the dual-camera system, and alignment of the two opposed cameras with their collimators to better than 1 mm accuracy. The capillary was moved in about 1 cm steps away from the Detector B towards Detector A. Individual and combined images were obtained from the two detectors. The combined images showed better resolution, which is to a large extent independent of the position of the capillary between the detector heads. The distances involved in the demonstration test (7 cm camera-to-camera spacing) were much shorter than in the case of head/neck imaging.

Additionally, from two opposed cameras and combined images were obtained of a frame formed from four >1 mm diameter capillaries. The frame, used to test alignment of the cameras, was placed in the middle plane between the two cameras and parallel to their surfaces. The combined image showed better resolution (narrow profiles of the capillary set) and higher contrast. The distances involved in this demonstration test (5 cm camera to camera spacing) were much shorter than in the realistic case of head/neck imaging.

Figure 6:
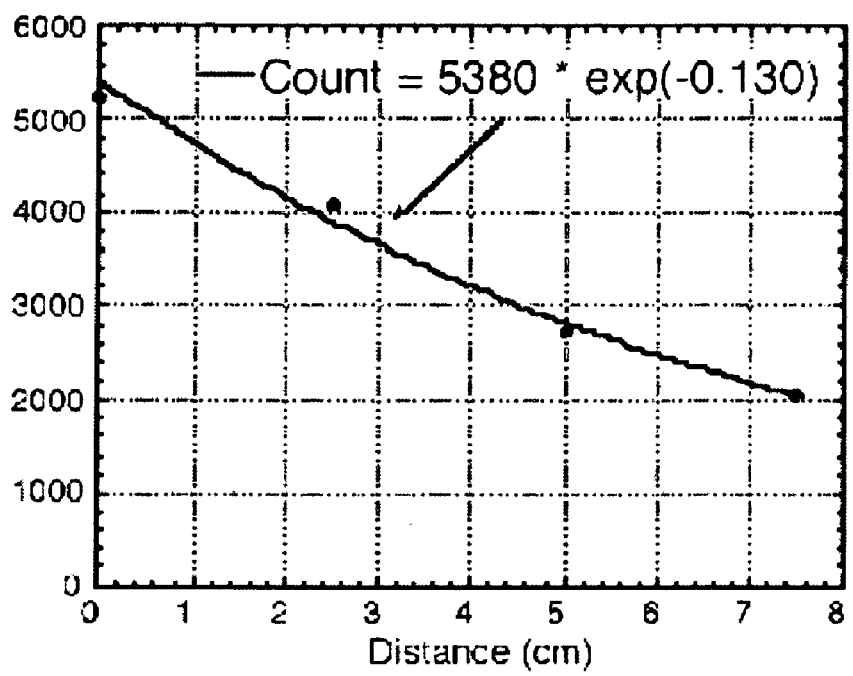
FIG. 6 is a graph of the dependence of detection sensitivity, expressed in counts per 10 minutes within lesion region-of-interest (ROI) as a function of lesion distance from the detector (in cm).

The results of imaging studies with small lesions in a warm background shows that combination of attenuation, scatter, and spatial resolution versus distance, each resulting in fractional losses to the lesion contrast, combine to produce significant signal reduction as a function of lesion-to-detector distance. The effects of attenuation with distance were studied first. FIG. 6 shows experimental detection sensitivity dependence of a simulated 9 mm diameter lesion in a small uniform gelatin phantom versus position of the lesion or thickness of overlaying "head tissue" between the lesion and the compact gamma camera's surface. In FIG. 6 the dependence of detection sensitivity is expressed in counts per 10 minutes within lesion region-of-interest (ROI) as a function of lesion distance from detector (in cm). A hot 9 mm diameter lesion in a cold breast phantom box filled with water was used. The observed approximately exponential decrease in signal of over a factor two in 5 cm of phantom material is due to absorption and scattering of 140 keV gamma rays emitted by the object sector or lesion. An attenuation coefficient of 0.130/cm was obtained in the exponential fit to the data points in FIG. 6. In the case of head or neck, the attenuation coefficient will be on average higher than in the soft tissue case, enhancing the distance effect. The above attenuation effects combine with the effects of distance on spatial (collimator) resolution to lower the contrast and signal-to-noise ratio (S/N) of the imaged lesions.

Figure 7:
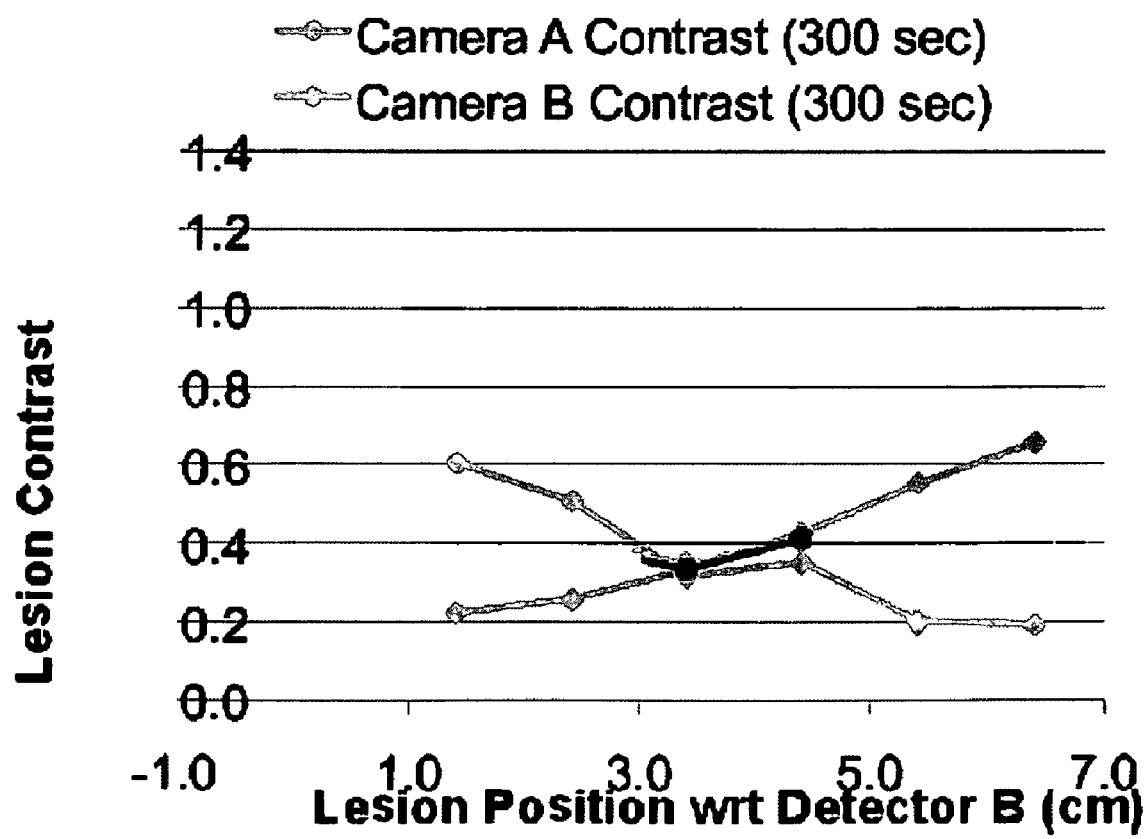
FIG. 7 is a graph of the lesion contrast of an 8 mm spherical lesion as measured individually by two opposed cameras and from combined (multiplied and summed) images versus position of the lesion between the detector heads.

In a further set of lesion/hot spot type studies, the contrast and S/N were studied for several lesions as a function of their position between two detector heads. As expected, in all lesion size and uptake cases, the contrast improved when combining the two opposite images, but this technique indeed showed its advantage by enhancing the visibility of small lesions. With reference to FIG. 7, there is depicted the lesion contrast of an 8 mm spherical lesion as measured individually by two opposed cameras and from combined (multiplied and summed) images versus position of the lesion between the detector heads. As can be seen, the contrast measured from combined multiplied images is over a factor two higher in this case, and is also to a large extent independent of the position of the lesion between the detector heads in a soft-tissue simulating 7 cm thick phantom. The distances involved in this demonstration test are much shorter than in the case of head/neck imaging.

The results of these experimental studies strongly suggest that the dual head system would offer better visibility of small structures in imaging the head/brain/neck. It is expected that these effects will be even more pronounced in the head/neck imaging cases with higher absorption coefficient and larger distances involved (25 cm over 10 cm).

A multi-compartment brain phantom, available from Data Spectrum Corporation of Hillsborough, N.C., was used in pilot studies with two detector heads placed at 21 cm distance. The top right "lobe" sector of the brain phantom was filled with about half activity, to simulate onset of Alzheimer's. The brain phantom was imaged with a two-head camera system with the cameras co-registered @180 degrees and the phantom placed on a rotating stage between the cameras to simulate SPECT operation of the system. Each camera used a 20×15 cm$^2$ FOV array of 3×3×6 mm$^3$ NaI(Tl) pixels (3.2 mm pitch) coupled to an array of 8×6 Hamamatsu R8520 PSP-MTs. The system used separate x (16) and y (12) readout sectors and an FPGA-based ADC DAQ system. For simplicity of the initial demonstration test, the phantom was placed parallel to the detector surfaces in the orthogonal orientation to what would be the proper patient's brain slice orientation in this imaging geometry.

Planar imaging tests were obtained using two opposed and co-registered gamma cameras. Images were obtained from the first camera, from the second camera, and combined images from the two cameras. A first set of images were obtained with the 2D brain phantom placed in the center plane between the two cameras spaced at 21 cm (surface-to-surface). A second set of images were obtained with the phantom placed against the first camera. Results showed the combined images were best in detecting the region of lowered activity in both of these extreme cases.

As shown in FIG. 5, and as expected in the case of single photon imaging (as opposed to PET imaging), spatial resolution deteriorates significantly with distance of the object element or sector from the parallel-hole collimator mounted on the detector head/gamma camera. Especially in the asymmetrical situation with the distances of the element or sector to the two cameras quite different, the effect is quite dramatic.

Additional brain phantom images were obtained with profiles across the top right "lobe" region with simulated low brain activity. The profiles obtained from combined images showed higher contrast in both imaging cases. In both cases, the contrast was improved when both images were combined. Other algorithms combining the two images are also possible with similar results, however it is unlikely that they will produce significantly larger contrast increase.

Trying to minimize this adverse effect usually results in serious reduction of imaging sensitivity, again in contrast to the PET imaging case. Therefore, an optimal approach involves utilizing the power of two combined imaging heads and obtain improved spatial resolution and image contrast, while maintaining high system sensitivity (but accompanied by poor spatial resolution imaging of the two individual heads).

In summary, in brain imaging cases when high sensitivity of the system is most important, the preferred option is to use high efficiency collimators with rather poor resolution performance at larger distances. For high spatial resolution applications two medium resolution collimators will suffice due to the strong combination effect characteristic of the proposed dual camera imaging method.

According to the present invention, a compact and mobile high resolution SPECT imaging system for imaging the head, brain, and neck areas of a patient includes two sets of two opposed and co-registered gamma cameras each. The four-head system is mounted on a rotating gantry, with cameras orbiting around the patient's head or neck. Due to their compactness, the edges of active FOVs of the neighboring camera heads are very close to the mechanical camera edges and this permits non-interfering and efficient camera positioning close to the patient's head/neck. Close positioning assures high spatial resolution in the compact and mobile high resolution SPECT imaging system.

Although the description above contains many specific descriptions, materials, and dimensions, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A compact and mobile high resolution single photon planar and SPECT brain imaging system for imaging the brain/neck/head of a patient that has been administered a single photon labeled biomarker comprising:
    a rotating gantry;
    two identical compact gamma imaging detector heads mounted on said rotating gantry and mechanically affixed on said gantry at an angle of 180 degrees relative to each other;
    said detector heads mechanically co-registered to each other at said 180° angle and maintaining said 180° alignment and co-registration during rotation of said gantry;
    said detector heads geometrically aligned to provide a one-to-one detector pixel correspondence between the two detectors;
    said detector heads placed on opposite sides of the patient's head with the patient's brain or neck fully encompassed by the resulting active field of view coverage of said detector heads;
    an arrangement to minimize head movements by the patient during imaging scans; and
    a data acquisition and processing system for accepting imaging data individually from each of said gamma detection modules and multiplying the pixel values of the two co-registered images obtained in the same time bin on a pixel-by-pixel basis to produce a single product image per each time bin.

2. The SPECT brain imaging system of claim 1 wherein said gamma imaging detector heads include
    two identical gamma cameras; and
    two identical and co-linear parallel-hole collimators.

3. The SPECT brain imaging system of claim 2 wherein said co-linear parallel-hole collimators mounted on said gamma cameras are precisely mechanically aligned with point and linear radioactive sources.

4. The SPECT brain imaging system of claim 2 wherein said detector heads include
    a scintillator as a sensor and energy converter of the gamma rays that pass through said parallel-hole collimators; and
    a photodetector to detect the scintillation light produced by the absorbed gamma rays in the scintillator.

5. The SPECT brain imaging system of claim 4 wherein
    said scintillator is constructed of pixelated or plate crystal materials selected from the group consisting of NaI(Tl), CsI(Tl), CsI(Na), GSO, and LaBr3; and
    said photodetector is selected from the group consisting of standard photomultiplier, multi-element photomultiplier, position sensitive photomultiplier, flat panel photomultiplier, microchannel plate based photomultiplier, avalanche photodiode array, large-size avalanche photodiode with resistive readout, and silicon photomultiplier.

6. The SPECT brain imaging system of claim 1 wherein the sensitivity of detection of a 9 mm lesion at a distance of 7 cm from the detector is at least 200 counts per minute/microcurie (cpm/μCi).

7. The SPECT brain imaging system of claim 1 wherein said gantry is capable of translational scan in addition to rotational scan.

8. The SPECT brain imaging system of claim 1 including a spatial resolution of at least 5 mm;
a width of imaging slice of 5-20 cm; and
a FOV of at least 20 cm×15 cm, said FOV fully encompassing the entire brain or neck of the patient.

9. The SPECT brain imaging system of claim 1 including an arrangement for adjusting the distance between said detector heads.

10. The SPECT brain imaging system of claim 1 wherein said single photon biomarker is selected from the group consisting of Tc-99m, I123, In111, Lu177, and I131.

11. The SPECT brain imaging system of claim 1 wherein said gantry is stepping or continuously rotating to produce two individually produced series of angular projections of the imaged region of the patient's head or neck in both of said co-registered detector heads.

12. The SPECT brain imaging system of claim 1 wherein said brain imaging system includes an imaging bed or chair; and
said arrangement to minimize head movements by the patient includes attaching the patient's head to said imaging bed or chair to minimize head movements while maintaining patient comfort.

13. The SPECT brain imaging system of claim 1 wherein, for a total radioactivity per unit time in the head/brain/neck segment of A, then following the simultaneous acquisition of the two planar images, the number of gamma rays detected by each camera 21 and 22 from that head/neck segment can be approximated by:

$$N_{21} = \epsilon_{21} t A \exp[-\mu d]$$

$$N_{22} = \epsilon_{22} t A \exp[-\mu(T-d)] \quad (1)$$

where $\epsilon_1$ and $\epsilon_2$ are the practical detection efficiencies of cameras 1 and 2 respectively, t is the acquisition time in seconds, μ is the linear attenuation coefficient of tissue in cm$^{-1}$, d is the depth in cm of the object sector under the surface of the head/neck and measured in the direction of the camera 1 surface, and T is the object thickness in the relevant projection plane and direction, in cm.

14. The SPECT brain imaging system of claim 13 wherein if the pixel values of the two co-registered images obtained in the same time bin are multiplied on a pixel-by-pixel basis, resulting in a single product image per each time bin, then the product image signal value from the object segment of interest can be approximated by the following formula:

$$N_{21} N_{22} = \epsilon_{21} \epsilon_{22} t^2 A^2 \exp[-\mu T]. \quad (2)$$

15. A compact and mobile high resolution single photon planar and SPECT brain imaging system for imaging the brain/neck/head of a patient that has been administered a single photon labeled biomarker comprising:
a rotating gantry including a ring plate;
two pairs of co-registered gamma detector heads mounted on said ring plate of said rotating gantry and mechanically affixed relative to each other to maintain a fixed angular orientation with respect to each other;
each detector head in each of said pairs of said detector heads mechanically affixed on said gantry relative and co-registered to each other at an angle of 180 degrees with respect to one another, said detector heads within each of said pairs of detector heads maintaining said 180° alignment and co-registration through rotation of said gantry;
said detector heads each of said pairs of detector heads geometrically aligned to provide a one-to-one detector pixel correspondence between the two detectors;
an adjustment arrangement for adjusting the positions and the relative angles between said pairs of detector heads;
said detector heads placed on opposite sides of the patient's head with the patient's brain or neck fully encompassed by the resulting active field of view coverage of said detector heads;
an arrangement to minimize head movements by the patient during imaging scans; and
a data acquisition and processing system for multiplying the pixel values of the two co-registered images obtained in each of said pairs in the same time bin on a pixel-by-pixel basis, resulting in a single product image per each time bin.

16. The SPECT brain imaging system of claim 15 wherein said two pairs of co-registered detector heads are mounted on said ring plate at 90 degree angles relative to one another.

17. The SPECT brain imaging system of claim 15 wherein said detector heads include a multi-pad PMT detector head arrangement operating with a rate capability of 250 kHz.

18. The SPECT brain imaging system of claim 15 wherein said gamma detector heads include
an array of 16 PMTs;
said PMTs arranged in a 4×4 array and coupled to a NaI(Tl) scintillator pixel array with 2 mm-5 mm pixel size; and
said PMTs are selected from the group consisting of flat panel multi-pad position sensitive PMTs and silicon PMTs.

19. The SPECT brain imaging system of claim 15 wherein said pairs of detector heads include silicon PMTs, collimators, shielding, and other materials, which are MRI-compatible and immune to magnetic fields thereby permitting insertion of said brain imaging system into an MRI magnet to achieve simultaneous dual-modality imaging including fMRI-SPECT.

* * * * *